United States Patent [19]

Edwards et al.

[11] Patent Number: 5,403,857
[45] Date of Patent: Apr. 4, 1995

[54] BENZENESULPHONAMIDE DERIVATIVES HAVING 5-LIPOXYGENASE INHIBITORY ACTIVITY

[75] Inventors: Philip N. Edwards, Bramhall; Keith Oldham, Poynton; David Waterson, Macclesfield, all of England

[73] Assignees: Imperial Chemical Industries PLC, London, England; ICI-Pharma, Cergy Cedex, France

[21] Appl. No.: 189,705

[22] Filed: Feb. 1, 1994

Related U.S. Application Data

[62] Division of Ser. No. 942,778, Sep. 10, 1992, Pat. No. 5,314,894.

[30] Foreign Application Priority Data

Sep. 10, 1991 [EP] European Pat. Off. ............ 91402404

[51] Int. Cl.6 ................... A61K 31/39; A61K 31/395; C07D 333/04; C07D 315/00
[52] U.S. Cl. ...................................... 514/432; 514/445; 514/446; 514/451; 514/471; 549/28; 549/62; 549/65; 549/67; 549/416; 549/417; 549/419; 549/423; 549/475; 549/476; 549/478
[58] Field of Search .......... 549/28, 62, 65, 67, 549/416, 417, 419, 423, 475, 476, 478; 514/432, 445, 446, 451, 471, 473

[56] References Cited

U.S. PATENT DOCUMENTS

| | | | |
|---|---|---|---|
| 5,098,930 | 3/1992 | Edwards et al. | 514/460 |
| 5,098,932 | 3/1992 | Hamon | 549/454 |
| 5,134,148 | 7/1992 | Carley et al. | 514/259 |
| 5,208,259 | 5/1993 | Bird et al. | 549/419 |
| 5,217,969 | 6/1993 | Bruneau et al. | 544/63 |
| 5,217,977 | 6/1993 | Crawley et al. | 514/311 |
| 5,221,677 | 6/1993 | Crawley et al. | 514/309 |
| 5,254,581 | 10/1993 | Bruneau et al. | 514/460 |

FOREIGN PATENT DOCUMENTS

| | | |
|---|---|---|
| 0375404 | 6/1990 | European Pat. Off. |
| 0385662 | 9/1990 | European Pat. Off. |
| 0409413 | 1/1991 | European Pat. Off. |
| 0420511 | 4/1991 | European Pat. Off. |
| 0488602 | 6/1992 | European Pat. Off. |
| 0495594 | 7/1992 | European Pat. Off. |

Primary Examiner—Mukund J. Shah
Assistant Examiner—Yogendra N. Gupta
Attorney, Agent, or Firm—Cushman Darby & Cushman

[57] ABSTRACT

The invention concerns benzenesulphonamide derivatives of the formula I

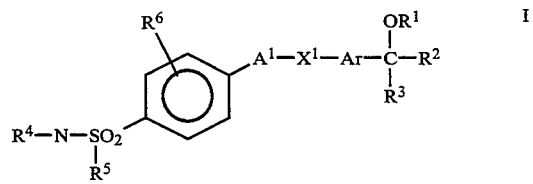

wherein $R^1$ is (1–4C)alkyl, (3–4C)alkenyl or (3–4C)alkynyl; $R^2$ and $R^3$ together form $-A^2-X^2-A^3-$ which defines a ring having 5 or 6 ring atoms, wherein $A^2$ and $A^3$ each is (1–3C)alkylene and $X^2$ is oxy, thio, sulphinyl or sulphonyl; $A^1$ is a direct link to $X^1$ or is (1–3C) alkylene; $X^1$ is oxy, thio or imino; Ar is optionally substituted phenylene; $R^4$ is (1–4C)alkyl, fluoro-(2–4C)alkyl or optionally substituted phenyl or a heterocyclic moiety; $R^5$ is hydrogen or (1–4C)alkyl; and $R^6$ is hydrogen, halogeno, trifluoromethyl, (1–4C)alkyl or (1–4C)alkoxy; or a pharmaceutically-acceptable salt thereof;

processes for their manufacture; pharmaceutical compositions containing them and their use as 5-lipoxygenase inhibitors.

6 Claims, No Drawings

BENZENESULPHONAMIDE DERIVATIVES HAVING 5-LIPOXYGENASE INHIBITORY ACTIVITY

This is a division of application No. 07/942,778, filed Sep. 10, 1992, now Pat. No. 5,314,894.

This invention concerns novel benzenesulphonamide derivatives and more particularly novel benzenesulphonamide derivatives which are inhibitors of the enzyme 5-lipoxygenase (hereinafter referred to as 5-LO). The invention also concerns processes for the manufacture of said benzenesulphonamide derivatives and novel pharmaceutical compositions containing them. Also included in the invention is the use of said benzenesulphonamide derivatives in the treatment of various inflammatory and/or allergic diseases in which the direct or indirect products of 5-LO catalysed oxidation of arachidonic acid are involved, and the production of new medicaments for such use.

As stated above the benzenesulphonamide derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, Z, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Applications Nos. 0375404, 0385662, 0409413 and 0420511 that certain heterocyclic derivatives possess inhibitory properties again 5-LO. Copending European Patent Application No. 91310784.3 (published as European Patent Application No. 0488602) is concerned with aryl derivatives which also possess inhibitory properties against 5-LO. Copending European Patent Application No. 92300236.4 (published as European Patent Application No. 0495594) is concerned with N-arylalkanesulphonamide derivatives which also possess inhibitory properties against 5-LO. We have now discovered that certain benzenesulphonamide derivatives which possess some structural features which are similar to those of the compounds disclosed in the above-mentioned applications but which possess other structural features, in particular a benzenesulphonamido substituent, which were not envisaged in those earlier applications, are effective inhibitors of the enzyme 5-LO and thus of leukotriene biosyntheses. Thus such compounds are of value as therapeutic agents in the treatment of, for example allergic conditions, psoriasis, asthma, cardiovascular and cerebrovascular disorders, and/or inflammatory and arthritic conditions, mediated alone or in part by one or more leukotrienes.

According to the invention there is provided a benzenesulphonamide derivative of the formula I (set out hereinafter) wherein $R^1$ is (1–4C)alkyl, (3–4C)alkenyl or (3–4C)alkynyl; and wherein $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ and $A^3$ which may be the same or different, each is (1–3C)alkylene and $X^2$ is oxy, thio, sulphinyl or sulphonyl, and which ring may bear one or two substituents, which may be the same or different, selected from hydroxy, (1–4C)alkyl and (1–4C)alkoxy; wherein $A^1$ is a direct link to $X^1$ or is (1–3C)alkylene; wherein $X^1$ is oxy, thio or imino; wherein Ar is phenylene which may optionally bear one or two substituents selected from halogeno, hydroxy, amino, trifluoromethyl, (1–4C)alkyl and (1–4C)alkoxy; wherein $R^4$ is (1–4C)alkyl or fluoro-(2–4C)alkyl, or $R^4$ is phenyl which may optionally bear one, two or three substituents selected from halogeno, hydroxy, amino, cyano, nitro, trifluoromethyl, carbamoyl, (1–4C)alkyl, (1–4C)alkoxy and (2–4C)alkanoylamino, or $R^4$ is a 5- or 6-membered monocyclic heterocyclic moiety or a 9- or 10-membered bicyclic heterocyclic moiety each containing one or two nitrogen heteroatoms and each optionally containing a further heteroatom selected from nitrogen, oxygen and sulphur, or a hydrogenated derivative thereof, which heterocyclic moiety may optionally bear one or two substituents selected from halogeno, hydroxy, amino, cyano, nitro, trifluoromethyl, carbamoyl, oxo, thioxo, (1–4C)alkyl, (1–4C)alkoxy and (2–4C)alkanoylamino; $R^5$ is hydrogen or (1–4C)alkyl; and $R^6$ is hydrogen, halogeno, trifluoromethyl, (1–4C)alkyl or (1–4C)alkoxy; or a pharmaceutically-acceptable salt thereof.

According to a further feature of the invention there is provided a benzenesulphonamide derivative of the formula I wherein $R^1$, $R^2$, $R^3$, $A^1$, $R^4$, $R^5$ and $R^6$ have any of the meanings defined hereinbefore and wherein $X^1$ is oxy, thio, sulphinyl, sulphonyl or imino; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $R^1$ when it is (1–4C)alkyl is, for example, methyl, ethyl, propyl or butyl; when it is (3–4C)alkenyl is, for example, allyl, 2-butenyl or 3-butenyl; and when it is (3–4C)alkynyl is, for example, 2-propynyl or 2-butynyl.

When $R^2$ and $R^3$ together form a group of the formula -$A^2$-$X^2$-$A^3$- which, together with the carbon atom to which $A^2$ and $A^3$ are attached, defines a ring having 5 or 6 ring atoms then a suitable value for $A^2$ and $A^3$ which may be the same or different, when each is (1–3C)alkylene is, for example, methylene, ethylene or trimethylene. Suitable values for the substituents which may be present on said 5- or 6-membered ring include for example:

for (1–4C)alkyl: methyl, ethyl, propyl, isopropyl, butyl and isobutyl;

for (1–4C)alkoxy: methoxy, ethoxy, propoxy, isopropoxy and butoxy.

A suitable value for $A^1$ when it is (1–3C)alkylene is, for example, methylene, ethylene or trimethylene.

A suitable value for Ar when it is phenylene is, for example, 1,3-phenylene or 1,4-phenylene.

A suitable value for a halogeno substituent which may be present on Ar is, for example, fluoro, chloro, bromo or iodo; for a (1–4C)alkyl substituent which may be present on Ar is, for example, methyl, ethyl, propyl, isopropyl, butyl, isobutyl, sec-butyl or tert-butyl; and for a (1–4C)alkoxy substituent which may be present on Ar is, for example, methoxy, ethoxy, propoxy, isopropoxy or butoxy.

A suitable value for $R^4$ when it is (1–4C)alkyl is, for example, methyl, ethyl, propyl, isopropyl, butyl, sec-butyl or tert-butyl; and when it is fluoro-(2–4C)alkyl is, for example, 2-fluoroethyl, 2,2-difluoroethyl or 2,2,2-trifluoroethyl.

Suitable values for substituents which may be present on $R^4$ when it is phenyl or a heterocyclic moiety include, for example:

for halogeno: fluoro, chloro, bromo and iodo;

for (1–4C)alkoxy: methoxy, ethoxy, propoxy, isopropoxy and butoxy;

for (1–4C)alkyl: methyl, ethyl, propyl, isopropyl, sec-butyl and tert-butyl;

for (2–4C)alkanoylamino: acetamido, propionamido and butyramido.

A suitable value for $R^4$ when it is a 5- or 6-membered monocyclic heterocyclic moiety or a 9- or 10-membered bicyclic heterocyclic moiety each containing one or two nitrogen heteroatoms and each optionally containing a further heteroatom selected from nitrogen, oxygen and sulphur, or a hydrogenated derivative thereof, is, for example, pyrrolyl, pyrrolidinyl, indolyl, pyrazolyl, indazolyl, imidazolyl, benzimidazolyl, oxazolyl, isoxazolyl, thiazolyl, isothiazolyl, 1,2,3-triazolyl, 1,2,4-triazolyl, oxadiazolyl, thiadiazolyl, pyridyl, quinolyl, isoquinolyl, pyrazinyl, pyrimidinyl, pyridazinyl, quinoxalinyl, quinazolinyl or cinnolinyl, which may be attached through any available position including through any available nitrogen atom and which may bear one or two substituents including a (1–4C)alkyl substituent on any available nitrogen atom. A particular value for is such a heterocyclic moiety which bears one $R^4$oxo or thioxo substituent, for example, 2-oxo-1,2-dihydropyridyl, 4-oxo-1,4-dihydropyridyl, 2-oxo-1,2-dihydroquinolinyl, 4-oxo-1,4-dihydroquinolinyl or 4-oxo-3,4-dihydroquinazolinyl, or the corresponding thioxo derivatives such as 2-thioxo-1,2-dihydropyridyl, which may be attached through any available position including through any available nitrogen atom and which may bear a further substituent including a (1–4C)alkyl substituent on any available nitrogen atom.

A suitable value for $R^5$ when it is (1–4C)alkyl is, for example, methyl, ethyl, propyl or butyl.

Suitable values for $R^6$ include, for example:

for halogeno: fluoro, chloro, bromo and iodo;

for (1–4C)alkyl: methyl, ethyl, propyl, isopropyl, butyl, isobutyl, sec-butyl and tert-butyl;

for (1–4C)alkoxy: methoxy, ethoxy, propoxy, isopropoxy and butoxy.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, benzenesulphonamide derivatives of the formula I wherein:

(a) $R^1$ is methyl, ethyl, allyl or 2-propynyl; and $R^2$ $R^3$ $A^1$ $X^1$, Ar, $R^4$ $R^5$ and $R^6$ have any of the meanings defined hereinbefore;

(b) $R^2$ and $R^3$ together form a group of the formula -$A^2$-$X^2$-$A^3$- which, together with the carbon atom to which $A^2$ and $A^3$ are attached, defines a ring having 5 or 6 ring atoms, wherein $A^2$ and $A^3$ which may be the same or different, each is methylene, ethylene or trimethylene and $X^2$ is oxy, and which ring may bear one or two substituents selected from hydroxy, methyl ethyl propyl methoxy and ethoxy; and $R^1$ $A^1$, $X^1$, Ar, $R^4$, $R^5$ and $R^6$ have any of the meanings defined hereinbefore:

(c) $A^1$ is a direct link to $X^1$ and $X^1$ is oxy or thio; and $R^1$, $R^2$, $R^3$, Ar $R^4$, $R^5$ and $R^6$ have any of the meanings defined hereinbefore;

(d) $A^1$ is methylene and $X^1$ is oxy or thio; and $R^1$, $R^2$, $R^3$, Ar $R^4$, $R^5$ and $R^6$ have any of the meanings defined hereinbefore;

(e) Ar is 1,3-phenylene or 1,4-phenylene which may optionally bear one or two substituents selected from fluoro, chloro, hydroxy, amino, trifluoromethyl, methyl and methoxy; and $A^1$, $X^1$, $R^1$, $R^2$, $R^3$, $R^4$, $R^5$ and $R^6$ have any of the meanings defined hereinbefore;

(f) $R^4$ is methyl, ethyl, propyl or 2,2,2-trifluoroethyl; and $R^1$, $R^2$, $R^3$, $A^1$, $X^1$, Ar $R^5$ and $R^6$ have any of the meanings defined hereinbefore;

(g) $R^4$ is phenyl which may bear one or two substituents selected from fluoro, chloro, cyano, nitro, trifluoromethyl, carbamoyl, methyl and methoxy; and $R^1$, $R^2$, $R^3$, $A^1$, $X^1$, Ar $R^5$ and $R^6$ have any of the meanings defined hereinbefore;

(h) $R^4$ is a 5- or 6-membered monocyclic heterocyclic moiety each containing one or two nitrogen heteroatoms and each optionally containing a further heteroatom selected from nitrogen, oxygen and sulphur, or a hydrogenated derivative thereof, which heterocylic moiety may optionally bear one or two substituents selected from fluoro, chloro, hydroxy, amino, cyano, nitro, trifluoromethyl, carbamoyl, methyl, ethyl, methoxy, ethoxy and acetamido; and $R^1$, $R^2$, $R^3$, $A^1$, $X^1$, Ar, $R^5$ and $R^6$ have any of the meanings defined hereinbefore;

(i) $R^4$ is pyrrolyl, pyrazolyl, imidazolyl, oxazolyl, thiazolyl, oxadiazolyl, thiadiazolyl, pyridyl, pyrazinyl, pyrimidinyl or pyridazinyl which may optionally bear one or two substituents selected from fluoro, chloro, hydroxy, amino, cyano, nitro, trifluoromethyl, carbamoyl, methyl ethyl, methoxy, ethoxy and acetamido; and $R^1$, $R^2$, $R^3$, $A^1$, $X^1$, Ar $R^5$ and $R^6$ have any of the meanings defined hereinbefore;

(j) $R^4$ is 2-thiazolyl, 1,3,4-thiadiazol-2-yl, 2-pyridyl, 3-pyridyl, 4-pyridyl or 2-pyrimidinyl which may optionally bear one or two substituents selected from chloro and methyl; and $R^1$, $R^2$, $R^3$, $A^1$, $X^1$, Ar $R^5$ and $R^6$ have any of the meanings defined hereinbefore;

(k) $R^5$ is hydrogen, methyl or ethyl; and $R^1$, $R^2$, $R^3$, $A^1$, $X^1$, Ar, $R^4$ and $R^6$ have any of the meanings defined hereinbefore;

(l) $R^5$ is hydrogen; and $R^1$, $R^2$, $R^3$, $A^1$, $X^1$, Ar, $R^4$ and $R^6$ have any of the meanings defined hereinbefore; or (m) $R^6$ is hydrogen, fluoro, chloro, trifluoromethyl, methyl or methoxy; and $R^1$, $R^2$, $R^3$, $A^1$, $X^1$, Ar $R^4$ and $R^5$ have any of the meanings defined hereinbefore.

A particular compound of the invention comprises a benzenesulphonamide derivative of the formula I wherein $R^1$ is methyl, ethyl or allyl; $R^2$ and $R^3$ together form a group of the formula -$A^2$-$X^2$-$A^3$- which, together with the carbon atom to which $A^2$ and $A^3$ are attached, defines a ring having 5 or 6 ring atom, wherein $A^2$ and $A^3$, which may be the same or different, each is methylene, ethylene or trimethylene and $X^2$ is oxy, and which ring may bear one or two substituents selected from methyl and ethyl; $A^1$ is a direct link to $X^1$, or is methylene; X is oxy or thio; Ar is 1,3-phenylene which may optionally bear one or two substituents selected from fluoro, chloro and trifluoromethyl; $R^4$ is methyl, ethyl or 2,2,2-trifluoroethyl, or $R^4$ is phenyl which may optionally bear one or two substituents selected from fluoro, chloro, cyano, nitro and trifluoromethyl, or $R^4$ is thiazolyl, thiadiazolyl, pyridyl or pyrimidinyl which may optionally bear one or two substituents selected from fluoro, chloro, hydroxy, amino, methyl and acetamido; $R^5$ is hydrogen or methyl; and $R^6$ is hydrogen, fluoro or chloro; or a pharmaceutically-acceptable salt thereof.

A preferred compound of the invention comprises a benzenesulphonamide derivative of the formula I wherein R is methyl; $R^2$ and $R^3$ together form a group of the formula -$A^2$-$X^2$-$A^3$- which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl substituent alpha to X2; $A^1$ is a direct link to $X^1$, or is methylene; $X^1$ is oxy or thio; Ar is 1,3-phenylene which may optionally bear 1 or 2 fluoro substituents; $R^4$ is methyl, ethyl or 2,2,2-trifluoroethyl, or $R^4$ is phenyl which may optionally bear one or two substituents selected from fluoro, chloro and nitro, or $R^4$ is 2-thiazolyl, 1,3,4-thiadiazol-2-yl, 2-pyridyl, 3-pyridyl, 4-pyridyl or 2-pyrimidinyl which may optionally bear one or two substituents selected from chloro and methyl; $R^5$ is hydrogen or methyl; and $R^6$ is hydrogen; or a pharmaceutically-acceptable salt thereof.

A further preferred compound of the invention comprises a benzenesulphonamide derivative of the formula I wherein $R^1$ is methyl; $R^2$ and $R^3$ together form a group of the formula -$A^2$-$X^2$-$A^3$- which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl substituent alpha to X2; $A^1$ is a direct link to $X^1$ is thio; Ar is 1,3-phenylene or 5-fluoro-1,3-phenylene; $R^4$ is 2-pyridyl, 5-chloropyrid-2-yl, 4,6-dimethylpyrimidin-2-yl, 2-thiazolyl or 1,3,4-thiadiazol-2-yl; $R^5$ is hydrogen; and $R^6$ is hydrogen; or a pharmaceutically-acceptable salt thereof.

A specific especially preferred compound of the invention is, for example, the following benzenesulphonamide derivative of the formula I, or a pharmaceutically-acceptable salt thereof: N-(5-chloropyrid-2-yl)-4-[3-(4-methoxytetrahydropyran-4-yl)phenylthio]benzenesulphonamide, N-(4,6-dimethylpyrimidin-2-yl)-4-[3-(4-methoxytetrahydropyran-4-yl)phenylthio]benzenesulphonamide, 4-[3-(4-methoxytetrahydropyran-4-yl)phenylthio]-N-(2-thiazolyl)benzenesulphonamide or 4-[3-(4-methoxytetrahydropyran-4-yl)phenylthio]-N-(1,3,4-thiadiazol-2yl)benzenesulphonamide.

A further specific especially preferred compound of the invention is, for example, the following benzenesulphonamide derivative of the formula I, or a pharmaceutically-acceptable salt thereof: N-(2-pyridyl)-4-[3-(4-methoxytetrahydropyran-4-yl)phenylthio]benzenesulphonamide or N-(5-chloropyrid-2-yl)-4-[5-fluoro-3-(4-methoxytetrahydropyran-4-yl)phenylthio]benzenesulphonamide.

A compound of the invention comprising a benzenesulphonamide derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated $R^1$, $R^2$, $R^3$, $A^1$, $X^1$, Ar $R^4$, $R^5$ and $R^6$ have any of the meanings defined hereinbefore.

(a) The coupling, conveniently in the presence of a suitable base, of a compound of the formula II with a compound of the formula III wherein Z is a displaceable group; provided that, when there is an amino or hydroxy group in Ar $R^2$ $R^3$ or $R^4$, any amino or hydroxy group may be protected by a conventional protecting group or alternatively any such group need not be protected, whereafter any undesired protecting group in Ar, $R^2$, $R^3$ and $R^4$ is removed by conventional means.

A suitable displaceable group Z is, for example, a halogeno or sulphonyloxy group, for example a chloro, bromo, iodo, methanesulphonyloxy or toluene-4-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, potassium butoxide, sodium hydroxide, potassium hydroxide, sodium hydride or potassium hydride. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 190° C., conveniently at or near ambient temperature.

A suitable protecting group for an amino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example by hydrogenation over a catalyst such as palladium-on-charcoal.

The starting materials of the formula II and of the formula III may be obtained by standard procedures of organic chemistry. The preparation of such starting materials is described within the accompanying non-limiting Examples which are provided for the purpose of illustration only. Alternatively necessary starting materials of the formula II are obtainable by analogous procedures to those illustrated in accompanying Scheme I (set out hereinafter) or by modifications thereto which are within the ordinary skill of an organic chemist.

A suitable protecting group $R^7$ as employed in Scheme I is any one of the many such groups known in the art and includes any appropriate protecting group as defined hereinbefore. Examples of such groups are given in Scheme I. The conditions for the introduction and removal of such protecting groups are described in standard textbooks or organic chemistry such as, for example, "Protective Groups in Organic Synthesis" by T W Green (J Wiley and Sons, 1981).

(b) Fox: the production of those compounds of the formula I wherein $A^1$ is a direct link to $X^1$ the coupling conveniently in the presence of a suitable base as defined hereinbefore, of a compound of the formula II with a compound of the formula IV wherein Z is a displaceable group as defined hereinbefore; provided that, when there is an amino or hydroxy group in Ar, $R^2$, $R^3$ or $R^4$ any amino or hydroxy group may be protected by a conventional protecting group as defined hereinbefore or alternatively any such group need not be protected, whereafter any undesired protecting group in Ar, $R^2$, $R^3$ and $R^4$ is removed by conventional means.

The coupling reaction is conveniently performed in a suitable inert solvent as defined hereinbefore and at a temperature in the range, for example, 10° to 190° C., conveniently at or near 120° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

The starting materials of the formula IV may be obtained by standard procedures of organic chemistry. The preparation of such starting materials is described within the accompanying non-limiting Examples which are provided for the purpose of illustation only.

(c) The coupling, conveniently in the presence of a suitable base as defined hereinbefore, of a compound of the formula V with a compound of the formula VI wherein Z is a displaceable group as defined hereinbefore; provided that, when there is an amino or hydroxy group in Ar, $R^2$, $R^3$ or $R^4$ any amino or hydroxy group may be protected by a conventional protecting group or alternatively any such group need not be protected, whereafter any undesired protecting group in Ar, $R^2$, $R^3$ and $R^4$ is removed by conventional means.

The coupling reaction is conveniently performed in a suitable inert solvent as defined hereinbefore and at a temperature in the range, for example, 10° to 190° C., conveniently at or near 120° C. The reaction may conveniently be performed in the presence of a suitable catalyst as defined hereinbefore.

The starting materials of the formula V and VI may be obtained by standard procedures of organic chemistry. Conveniently intermediates of the formula VI wherein Z, Ar, $R^1$, $R^2$ and $R^3$ have the meanings defined hereinbefore, may be obtained by way of compounds of the formula Z-Ar-Y, wherein Z and Ar have the meanings defined hereinbefore and Y is, for example, a halogeno, formyl, alkanoyl, nitrile or alkoxycarbonyl group, as illustrated in accompanying Scheme II (set out hereinafter). It will also be appreciated that the intermediate of the formula VI may conveniently be obtained from the compound of the formula Z-Ar-Y, as defined hereinbefore, by reversing the order of introduction of the groups $R^2$ and $R^3$ which is used in Scheme II.

(d) The alkylation, conveniently in the presence of a suitable base as defined hereinbefore, of a compound of the formula VII with a compound of the formula $R^1$-Z, wherein $R^1$ and Z have the meanings defined hereinbefore; provided that, when there is an amino, imino or hydroxy group in Ar, $R^2$, $R^3$ or $R^4$ any amino, imino or hydroxy group may be protected by a conventional protecting group or alternatively any such group need not be protected, whereafter any undesired protecting group in Ar, $R^2$, $R^3$ and $R^4$ is removed by conventional means A suitable protecting group for an imino group is, for example, any of the suitable protecting groups for an amino group as disclosed hereinbefore.

The tertiary alcohol starting material of the formula VII may be obtained by standard procedures of organic chemistry. Conveniently, and as illustrated in accompanying Scheme III (set out hereinafter), suitable formyl, alkanoyl, nitrile or alkoxycarbonyl compounds may be utilised in the preparation of the tertiary alcohol starting material of the formula VII.

(e) For the production of those compounds of the formula I wherein $X^1$ is a sulphinyl or sulphonyl group, or $R^2$ and $R^3$ together form a group of the formula $-A^2-X^2-A^3-$ and $X^2$ is a sulphinyl or sulphonyl group, the oxidation of a compound of the formula I wherein $X^1$ is a thio group, or $R^2$ and $R^3$ together form a group of the formula $-A^2-X^2-A^3-$ and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formula VII, and these are provided as a further feature of the invention.

As stated previously, the novel compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of LTB$_4$ using specific radioimmunoassays described by Carey and Forder (*Prostaglandins, Leukotrienes Med.*, 1986, 2-2, 57; *Prostaglandins*, 1984, 28, 666; *Brit. J. Pharmacol.*, 1985, 84, 34P) which involve the use of a protein-LTB$_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane B$_2$(TxB$_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of LTB$_4$ and TxB$_2$. This test provides an indication of the bioavailability of a test compound as an inhibitor of 5-LO or cyclooxygenase.

c) An in vivo system involving measuring the effects of a test compound administered orally against the liberation of LTB$_4$ induced by zymosan within an air pouch generated within the subcutaneous tissue of the back of male rats. The rats are anaesthetised and air pouches are formed by the injection of sterile air (20ml). A further injection of air (10ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1ml of a 1% suspension in physiological saline). After 3 hours the rats are killed, the air pouches are lavaged with physiological saline, and the specific radioimmunoassay described above is used to assay LTB$_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)-c):

Test a): IC$_{50}$ (LTB$_4$) in the range, for example, 0.01–40μM IC$_{50}$ (TxB$_2$) in the range, for example, 40–200μM;

Test b): oral ED$_{50}$(LTB$_4$) in the range, for example, 1–100mg/kg;

Test c): oral ED$_{50}$(LTB$_4$) in the range, for example, 0.5–50mg/kg.

No overt toxicity or other untoward effects are present in tests b) and/or c) when compounds of the formula I are administered at several multiples of their minimum inhibitory dose or concentration.

Thus, by way of example, the compound N-(5-chloropyrid-2-yl)-4-[3-(4-methoxytetrahydropyran-4-yl)phenylthio]benzenesulphonamide has an IC$_{50}$ of 4.2μM against LTB$_4$ in test a), and an oral ED$_{50}$ of 1.5mg/kg versus LTB$_4$ in test c); and the compound 4-[3-(4-methoxytetrahydropyran-4-yl)phenylthio]-N-(2-thiazolyl)benzenesulphonamide has an IC$_{50}$ of 1μM against LTB$_4$ in test a), and an oral ED$_{50}$ of 1.5mg/kg versus LTB$_4$ in test c). In general those compounds of the formula I which are particularly preferred have an IC$_{50}$ of <10μM against LTB$_4$ in test a) and an oral ED$_{50}$ of <100 mg/kg against LTB$_4$ in tests b) and/or c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a benzenesulphonamide derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder, for example a dry powder or a microcrystalline form, or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a benzenesulphonamide derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a benzenesulphonamide derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrtenes, the production of which is mediated by 5-LO. As previously mentioned, such conditions include, for example, asthmatic conditions, allergic reactions, allergic thiniris, allergic shock, psoriasis, atopic dermatitis, cardiovascular and cerebrovascular disorders of an inflammatory nature, arthrttic and inflammatory joint disease, and inflammatory bowel diseases.

In using a compound of the formula I for therapeutic or prophylactic purposes it will generally be administered so that a daily dose in the range, for example, 0.5 mg to 75mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotecttve effects, for example they are useful in reducing or suppressing certain of the adverse gastrointestinal effects of the cyclooxygenase inhibitory nonsteroidal anti-inflammatory agents (NSAIA), such as indomethacin, acetylsalicylic acid, tbuprofen, sultndac, rolmerin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a benzenesulphonamide derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the structures of the end-products of the formula I were confirmed by NMR and mass spectral techniques; unless otherwise stated, CDCl3 solutions of the end-products of the formula I were used for the determination of the NMR spectral data, chemical shift values were measured on the delta scale; the following abbreviations have been used: s, singlet; d, doublet; t, triplet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:
THF tetrahydrofuran;
DHF N,N-dimethylformamide.

EXAMPLE 1

A mixture of a 1:1 mixture (0.954 E) of 4-bromomethyl-N,N-dimethylbenzenesulphonamide and N,N-dimethyl-4-toluenesulphonamide, 4-(3-hydroxyphenyl)-4-methoxytetrahydropyran (European Patent Application No. 0385662; 0.416 g), potassium carbonate (0.69 g) and DMF (20 ml) was stirred at ambient temperature for 16 hours. The mixture was evaporated and the residue was partitioned between methylene chloride and water. The organic phase was washed with brine, dried (MESO4) and evaporated. The residue was purified by column chromatography using a 1:1 v/v mixture of hexane and ethyl acetate as eluent. There was thus obtained 4-[3-(4-methoxytetrahydropyran-4-yl)phenoxymethyl]-N,N-dimethylbenzenesulphonamide (0.443 g, 55%), m.p. 125°–126° C.

The sulphonamide starting material mixture was obtained as follows: An aqueous solution of dimethylamine (40% w/v, 26.25 ml) was added dropwise to a stirred solution of 4-toluenesulphonyl chloride (19.05 g) in THF (50 ml) and the mixture was cooled in a water bath to keep the temperature of the reaction mixture below 40° C. The mixture was stirred at ambient temperature for 70 hours. The mixture was partitioned between ethyl acetate and 2N aqueous hydrochloric acid solution. The organic phase was washed with water and with brine, dried (MgSO4) and evaporated. There was thus obtained N,N-dimethyl-4-toluenesulphonamide (19 g). A mixture of a portion (9.95 g) of the product so obtained, N-bromosuccinimide (8.9 g), 2,2'-azobisisobutyronitrile (0.017 g) and carbon tetrachloride (175 ml) was stirred and heated to reflux for 90 minutes. The mixture was cooled to ambient temperature and filtered. The filtrate was washed with water, with a saturated aqueous sodium dithionite solution and with brine, dried (MgSO4) and evaporated. The residue was purified by column chromatography using a 2:1 v/v mixture of hexane and ethyl acetate as eluent. There was thus obtained an amorphous solid which was shown by proton magnetic resonance spectroscopy to be a 1:1 mixture (7.37 g) of 4-bromomethyl-N,N-dimethylbenzenesulphonamide and N,N-dimethyl-4-toluenesulphonamide.

EXAMPLE 2

A mixture of N-(4-fluorophenyl)-4-iodobenzenesulphonamide (0.38 g), 4-methoxy-4-(3-mercaptophenyl)-tetrahydropyran (European Patent Application No. 0420511; 0.25 g), cuprous chloride (0.015 g), potassium carbonate (0.15 g) and DMF (3 ml) was stirred and heated to 120° C. for 1 hour. The mixture was cooled to ambient temperature, water (15 ml) was added and the mixture was extracted with diethyl ether (2×20 ml). The combined extracts were washed with water and with brine, dried (HgSO4) and evaporated. The residue was purified by column chromatography using increasingly polar mixtures of hexane and ethyl acetate as eluent. There was thus obtained N-(4-fluorophenyl)4-[3-(4-methoxytetrahydropyran-4-yl)phenylthio]benzenesulphonamide (0.15 g, 30%), m.p. 165°–166° C. (recrystallised from ethyl acetate). NMR Spectrum 1.95 (m, 4H), 2.97 (s, 3H), 3.81 (m, 4H), 6.54 (s, 1H), 6.88–7.09 (m, 4H), 7.13 (d, 2H), 7.42 (m, 3H), 7.54 (m, 3H).

The N-(4-fluorophenyl)-4-iodobenzenesulphonamide used as a starting material was obtained as follows: 4-Iodobenzenesulphonyl chloride (4.1 g) was added portionwise to a stirred mixture of 4-fluoroaniline (1 g), potassium carbonate (1.86 g) and DMF (20 ml) and the mixture was stirred at ambient temperature for 3 hours. Water (80 ml) was added and the mixture was extracted with ethyl acetate (3×40 ml). The combined extracts were washed with dilute aqueous hydrochloric acid, with water, with a saturated aqueous sodium bicarbonate solution, with water and with brine, dried (Na2SO4) and evaporated. The residue was triturated under ethyl acetate, filtered and the filtrate was evaporated. The residue was purified by column chromatography using increasingly polar mixtures of hexane and ethyl acetate as eluent. There was thus obtained the required starting material (1.5 g), m.p. 148°–150° C. NMR Spectrum 6.56 (s, 1H), 6.9–7.1 (m, 4H), 7.4 (d, 2H), 7.8 (d, 2H).

EXAMPLE 3

The procedure described in Example 2 was repeated except that 4-iodo-N-(4-nitrophenyl)benzenesulphonamide was used in place of N-(4-fluorophenyl)-4-iodobenzenesulphonamide. There was thus obtained 4-[3-(4-methoxytetrahydropyran-4-yl)phenylthio]-N-(4-nitrophenyl)benzenesulphonamide in 38% yield, m.p. 163.5°–164.5° C. NMR Spectrum 1.95 (m, 4H), 2.97 (s, 3H), 3.84 (m, 4H), 7.17 (d, 2H), 7.24 (d, 2H), 7.32 (s, 1H), 7.4–7.5 (m, 3H), 7.53 (d, 1H), 7.69 (d, 2H), 8.13 (d, 2H).

The 4-iodo-N-(4-nitrophenyl)benzenesulphonamide used as a starting material was obtained from 4-nitroaniline using an analogous procedure to that described in the portion of Example 2 which is concerned with the preparation of starting materials except that acetic acid was used in place of DMF as the reaction solvent, that sodium acetate (0.5 equivalents relative to 4-nitroaniline) was added and that the reaction mixture was heated to 100° C. for 1 hour. There was thus obtained the required starting material in 13% yield. NMR Spectrum 7.22 (d, 2H), 7.57 (d, 2H), 7.87 (d, 2H), 8.16 (d, 2H).

EXAMPLE 4

The procedure described in Example 2 was repeated except that N-(5-chloropyrid-2-yl)-4-iodobenzenesulphonamide was used in place of N-(4-fluorophenyl)-4-iodobenzenesulphonamide and that, after the reaction mixture was cooled to ambient temperature, water was added, the mixture was acidified to pH6 by the addition of dilute aqueous hydrochloric acid and the mixture was extracted with methylene chloride. There was thus obtained N-(5-chloropyrid-2-yl)-4-[3-(4-methoxytetrahydropyran-4-yl)phenylthio]benzenesulphonamide in 5% yield, m.p. 155°–156° C. NMR Spectrum (CD$_3$SOCD$_3$) 1.9 (m, 4H), 2.86 (s, 3H), 3.67 (m, 4H), 7.05 (d, 1H), 7.29 (d, 2H), 7.37–7.53 (m, 4H), 7.73–7.87 (m, 3H), 8.2 (d, 1H), 11.2 (s, 1H).

The N-(5-chloropyrid-2-yl)-4-iodobenzenesulphonamide used as a starting material was obtained from 5-chloro-2-aminopyridine using an analogous procedure to that described in the portion of Example 2 which is concerned with the preparation of starting materials except that pyridine was used in place of DMF as the reaction solvent and the reaction mixture was heated to 50° C. for 2 hours. There was thus obtained the required starting material in 35% yield. NMH Spectrum (CD$_3$SOCD$_3$) 7.07 (d, 1H), 7.66 (m, 2H), 7.8 (m, 1H), 7.96 (m, 2H), 8.2 (d, 1H), 11.4 (s, 1H).

EXAMPLE 5

The procedure described in Example 2 was repeated except that N-(4,6-dimethylpyrimidin-2-yl)-4-iodobenzenesulphonamide was used in place of N-(4-fluorophenyl)-4-iodobenzenesulphonamide- There was thus obtained N-(4,6-dimethylpyrimidin-2-yl)-4-[3-(4-methoxytetrahydropyran-4-yl)phenylthio]benzenesulphonamide in 15% yield, m.p. 171.5–173° C. (recrystallised from ethyl acetate). NMR Spectrum (CD$_3$SOCD$_3$) 1.85 (m, 4H), 2.25 (s, 6H), 2.85 (s, 3H), 3.7 (m, 4H), 6.7 (s, 1H), 7.3 (d, 2H), 7.45 (d, 2H), 7–9 (d, 2H).

The N-(4,6-dimethylpyrimidin-2-yl)-4-iodobenzenesulphonamide used as a starting material was obtained from 4,6-dimethyl2-aminopyrimidine using an analogous procedure to that used in the portion of Example 2 which is concerned with the preparation of starting materials except that pyridine was used in place of DMF as the reaction solvent and that the reaction mixture was heated to 45° C. for 18 hours. There was thus obtained the required starting material in 58% yield. NMR Spectrum (CD$_3$SOCD$_3$) 2.25 (s, 6H), 6.75 (s, 1H), 7.7 (d, 2H), 7.9 (d, 2H), 12.0 (broad s, 1H).

EXAMPLE 6

The procedure described in Example 2 was repeated except that 4-iodo-N-(2-thiazolyl)benzenesulphonamide was used in place of N-(4-fluorophenyl)-4-iodobenzenesulphonamide. There was thus obtained 4-[3-(4-methoxytetrahydropyran-4-yl)phenylthio]-N-(2-thiazolyl)benzenesulphonamide in 13% yield, m.p. 166°–168° C. (recrystallised from a mixture of hexane and ethyl acetate). NMR Spectrum (CD$_3$SOCD$_3$) 1.9 (m, 4H), 2.9 (s, 3H), 3.7 (m, 4H), 6.8 (s, 1H), 7.25 (s, 1H), 7.3 (d, 2H), 7.45 (m, 4H), 7.7 (d, 2H).

The 4-iodo-N-(2-thiazolyl)benzenesulphonamide used as a starting material was obtained from 2-aminothiazole using an analogous procedure to that used in the portion of Example 2 which is concerned with the preparation of starting materials except that pyridine was used in place of DMF as the reaction solvent and that the reaction mixture was stirred at ambient temperature for 48 hours. There was thus obtained the required starting material in 70% yield. NMR Spectrum (CD$_3$SOCD$_3$) 6.8 (d, 2H), 7.25 (d, 2H), 7.55 (d, 2H), 7.9 (d, 2H), 12.8 (broad s, 1H).

EXAMPLE 7

The procedure described in Example 2 was repeated except that 4-iodo-N-(1,3,4-thiadiazol-2-yl)benzenesulphonamide was used in place of N-(4-fluorophenyl)-4-iodobenzenesulphonamide and that the chromatography solvent involved increasingly polar mixtures of hexane, ethyl acetate and acetic acid. There was thus obtained 4-[3-(4-methoxytetrahydropyran-4-yl)phenylthio]-N-(1,3,4-thiadiazol-2yl)benzenesulphonamide in 10% yield, m.p. 194°–196° C. (recrystallised from ethyl acetate). NMR Spectrum 2.0 (m, 4H), 2.5 (s, 3H), 3.0 (s, 3H), 3.8 (m, 4H), 7.2 (d, 2H), 7.4 (m, 3H), 7.5 (s, 1H), 7.7 (d, 2H), 10.3 (broad s, 1H).

The 4-iodo-N-(1,3,4-thiadiazol-2-yl)benzenesulphonamide used as a starting material was obtained from 2-amino-1,3,4-thiadiazole using an analogous procedure to that used in the portion of Example 2 which is concerned with the preparation of starting materials except that pyridine was used in place of DMF as the reaction solvent and that the reaction mixture was stirred at ambient temperature for 24 hours and then heated to 40° C. for 4 hours. There was thus obtained the required starting material in 30% yield. NMR Spectrum (CD$_3$SOCD$_3$) 2.5 (s, 3H), 7.55 (d, 2H), 7.9 (d, 2H).

EXAMPLE 8

The procedure described in Example 2 was repeated except that N-(4-fluorophenyl)-N-methyl-4-iodobenzenesulphonamide was used in place of N-(4-fluorophenyl)-4-iodobenzenesulphonamide. There was thus obtained N-(4-fluorophenyl)-4-[3-(4-methoxytetrahydropyran-4-yl)phenylthio]-N-methylbenzenesulphonamide in 80% yield as a gum. NMR Spectrum (CD$_3$SOCD$_3$) 2.0 (m, 4H), 3.0 (s, 3H), 3.15 (s, 3H), 3.85 (m, 4H), 6.9–7.55 (m, 12H).

The N-(4-fluorophenyl)-N-methyl-4-iodobenzenesulphonamide used as a starting material was obtained as follows:

Sodium hydride (60% dispersion in mineral oil, 0.08 g) was added to a stirred mixture of N-(4-fluorophenyl)-4-iodobenzenesulphonamide (0.5 g) and DMF (3 ml) and the mixture was stirred at ambient temperature for 45 minutes. Hethyl iodide (0.25 ml) was added and the mixture was stirred at ambient temperature for 5 hours. The mixture was poured into water (15 ml) and extracted with ethyl acetate (3×10 ml). The combined extracts were washed with water, dried (Na$_2$SO$_4$) and evaporated. The residue was purified by column chromatography using increasingly polar mixtures of hexane and ethyl acetate as eluent. There was thus obtained the required starting material in 64% yield as a solid. NMR Spectrum: 3.15 (s, 3H), 7.0 (m, 4H), 7.25 (m, 2H), 7.8 (m, 2H).

EXAMPLE 9

The procedure described in Example 2 was repeated except that N-(2,4-difluorophenyl)-4-iodobenzenesulphonamide was used in place of N-(4-fluorophenyl)-4-iodobenzenesulphonamide. There was thus obtained N-(2,4-difluorophenyl)-4-[3-(4-methoxytetrahydropyran-4-yl)phenylthio)benzenesulphonamide in 25% yield, m.p. 182°–183° C. NMR Spectrum: (CD$_3$SOCD$_3$) 1.9 (m, 4H), 2.9 (s, 3H), 3.7 (m, 4H), 7.0–7.6 (m, 11H), 10.1 (broad s, 1H).

The N-(2,4-difluorophenyl)-4-iodobenzenesulphonamide used as a starting material was obtained from 2,4-difluoroaniline using an analogous procedure to that described in the portion of Example 4 which is concerned with the preparation of starting materials. There was thus obtained the required starting material in 85% yield. *NMR Spectrum:* 6.5 (broad s, 1H), 6.7–6.9 (m, 2H), 7.4–7.6 (m, 3H), 7.8 (m, 2H).

EXAMPLE 10

The procedure described in Example 2 was repeated except that 4-iodo-N-(2,2,2-trifluoroethyl)benzenesulphonamide was used in place of N-(4-fluorophenyl)-4-iodobenzenesulphonamde except that, after the reaction mixture had been cooled to ambient temperature, the mixture was acidified to pH3 by the addition of dilute aqueous hydrochloric acid prior to extraction with diethyl ether. There was thus obtained 4-[3-(4-methoxytetrahydropyran-4-yl)phenylthio]-N-(2,2,2trifluoroethyl)benzenesulphonamide in 50% yield as a gum. *NMR Spectrum:* 2.0 (m, 4H), 3.0 (s, 3H), 3.65 (m, 2H), 3.85 (m, 4H), 4.9 (broad t, 1H), 7.25 (m, 2H), 7.45 (m, 3H), 7.55 (m, 1H), 7.7 (m, 2H).

The 4-iodo-N-(2,2,2-trifluoroethyl)benzenesulphonamide used as a starting material was obtained from 2,2,2-trifluoroethylamine using an analogous procedure to that described in the portion of Example 2 which is concerned with the preparation of starting materials. There was thus obtained the required starting material in 8% yield. *NMR Spectrum:* 3.7 (m, 2H), 4.9 (broad t, 1H), 7.6 (d, 2H), 7.9 (d, 2H).

EXAMPLE 11

The procedure described in Example 2 was repeated except that N-(2-pyridyl)-4-iodobenzenesulphonamide was used in place of N-(4-fluorophenyl)-4-iodobenzenesulphonamide. There was thus obtained N-(2-pyridyl)-4-[3-(4-methoxytetrahydropyran-4-Yl)phenylthio]benzenesulphonamide in 32% yield, m.p. 139°–140° C. *NMR Spectrum:* (CD$_3$SOCD$_3$) 1.9 (m, 4H), 2.85 (s, 3H), 3.7 (m, 4H), 6.85 (t, 1H), 7.13 (d, 1H), 7.3 (d, 2H), 7.4 (m, 4H), 7.7 (m, 1H), 7.78 (d, 2H), 8.0 (d, 1H).

The N-(2-pyridyl)-4-iodobenzenesulphonamide used as a starting material was obtained from 2-aminopyridine using an analogous procedure to that described in the portion of Example 4 which is concerned with the preparation of starting materials. There was thus obtained the required starting material in 81% yield. *NMR Spectrum:* 6.8 (t, 1H), 7.25 (d, 1H), 7.6 (m, 1H), 7.68 (d, 2H), 7.8 (d, 2H), 8.0 (m, 1H).

EXAMPLE 12

The procedure described in Example 4 was repeated except that 4-(5-fluoro-3-mercaptophenyl)-4-methoxytetrahydropyran (European Patent Application No. 0420511, Example 4 thereof) was used in place of 4-methoxy-4-(3-mercaptophenyl)tetrahydropyran. There was thus obtained N-(5-chloropyrid-2-yl)-4-[5-fluoro-3-(4-methoxytetrahydropyran-4ylphenylthio]benzenesulphonamide in 22% yield, m.p. 170°–171° C. *NMR Spectrum:* 1.9 (m, 4H), 3.0 (s, 3H), 3.8 (m, 4H), 7.0–7.3 (m, 6H), 7.38 (d, 1H), 7.6 (q, 1H), 7.7 (d, 2H), 8.3 (d, 1H).

EXAMPLE 13

The procedure described in Example 2 was repeated except that N-(4-pyridyl)-4-iodobenzenesulphonamide was used in place of N-(4-fluorophenyl)-4-iodobenzenesulphonamide. There was thus obtained N-(4-pyridyl)-4-[3-(4-methoxytetrahydropyran-4-Yl)PhenYlthio]benzenesulphonamide in 16% yield, m.p. 197°–199° C. *NMR Spectrum:* (CD$_3$SOCD$_3$) 1.9 (m, 4H), 2.85 (s, 3H), 3.7 (m, 4H), 6.9 (broad d, 2H), 7.25 (d, 2H), 7.4 (m, 4H), 7.7 (d, 2H), 8.0 {broad, s, 2H), 14.8 (broad s, 1H).

The N-(4-pyridyl)-4-iodobenzenesulphonamide used as a starting material was obtained from 4-aminopyridine using an analogous procedure to that described in the portion of Example 4 which is concerned with the preparation of starting materials. There was thus obtained the required starting material in 32% yield. *NMR Spectrum:* (CD$_3$SOCD$_3$) 7.3 (d, 2H), 7.7 (d, 2H), 8.0 (d, 2H), 8.85 (d, 2H).

EXAMPLE 4

The procedure described in Example 10 was repeated except that N-(3-pyridyl)-4-iodobenzenesulphonamide was used in place of 4-iodo-N-(2,2,2-trifluoroethyl)benzenesulphonamide. There was thus obtained N-(3-pyridyl)-4-[3-(4-methoxytetrahydropyran-4-yl)phenylthio]benzenesulphonamide in 18% yield, m.p. 191°–193° C. *NMR Spectrum:* 1.9 (m, 4H), 2.85 (s, 3H), 3.7 (m, 4H), 7.3 (d, 2H), 7.5 (m, 6H), 7.7 (d, 2H), 10.5 (broad s, 1H).

The N-(3-pyridyl)-4-iodobenzenesulphonamide used as a starting material was obtained from 3-aminopyridine using an analogous procedure to that described in the portion of Example 4 which is concerned with the preparation of starting materials. There was thus obtained the required starting material in 63% yield. *NMR Spectrum:* (CD$_3$SOCD$_3$) 7.3 (m, 1H), 7.5 (d, 2H), 7.95 (d, 2H), 8.25 (d, 2H), 10.6 (broad s, 1H).

EXAMPLE 15

The procedure described in Example 10 was repeated except that N-(2-pyrimidinyl)-4-iodobenzenesulphonamide was used in place of 4-iodo-N-(2,2,2-trifluoroethyl)benzenesulphonamide. There was thus obtained N-(2-pyrimidinyl)-4-[3-(4-methoxytetrahydropyran-4-yl)phenylthio]benzenesulphonamide in 13% yield, m.p. 195°–197° C. *NMR Spectrum:* 2.0 (m, 4H), 3.0 (s, 3H), 3.8 (m, 4H), 7.0 (t, 1H), 7.2 (d, 2H), 7.45 (m, 3H), 7.53 (s, 1H), 8.0 (d, 2H), 8.6 (d, 2H), 11.2 (broad s, 1H).

The N-(2-pyrimidinyl)-4-iodobenzenesulphonamide used as a starting material was obtained from 2-aminopyrimidine using an analogous procedure to that described in the portion of Example 4 which is concerned with the preparation of starting materials. There was thus obtained the required starting material in 57% yield. *NMR Spectrum:* (CD$_3$SOCD$_3$) 7.05 (t, 1H), 7.7 (d, 2H), 7.95 (d, 2H), 8.5 (d, 2H), 11.9 (broad s, 1H).

CHEMICAL FORMULAE

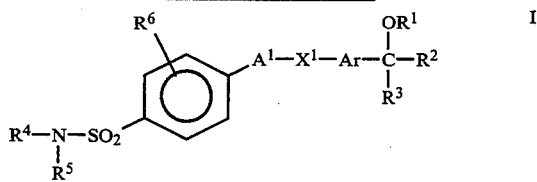

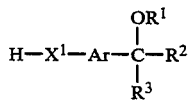

CHEMICAL FORMULAE
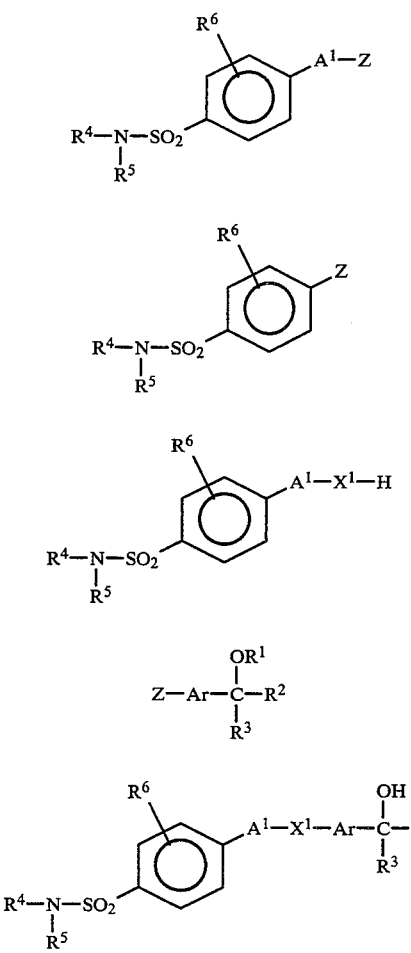
SCHEME I
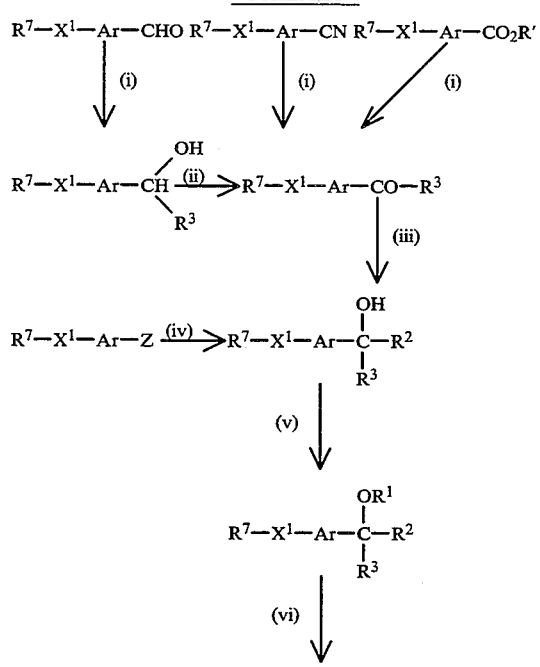
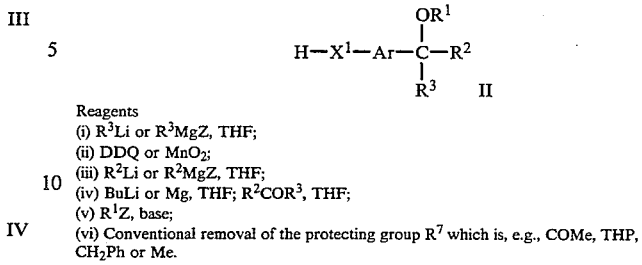
Reagents
(i) $R^3Li$ or $R^3MgZ$, THF;
(ii) DDQ or $MnO_2$;
(iii) $R^2Li$ or $R^2MgZ$, THF;
(iv) BuLi or Mg, THF; $R^2COR^3$, THF;
(v) $R^1Z$, base;
(vi) Conventional removal of the protecting group $R^7$ which is, e.g., COMe, THP, $CH_2Ph$ or Me.
SCHEME II
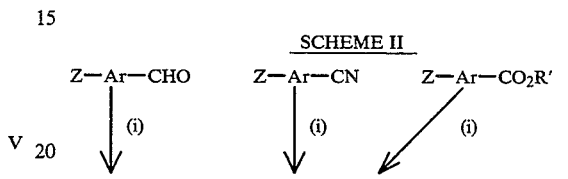
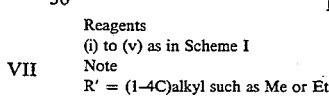
Reagents
(i) to (v) as in Scheme I
Note
R' = (1–4C)alkyl such as Me or Et
SCHEME III
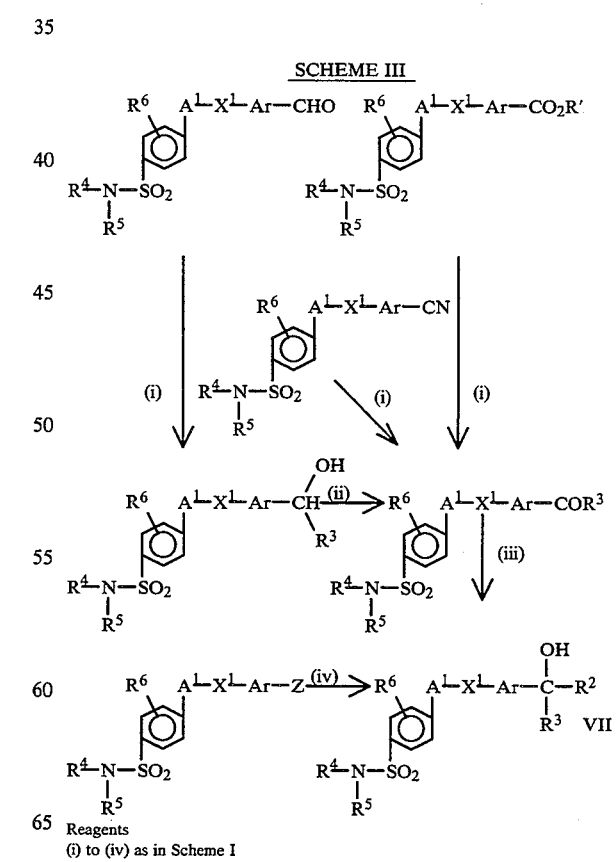
Reagents
(i) to (iv) as in Scheme I
What we claim is:

1. A benzenesulphonamide derivative of the formula I

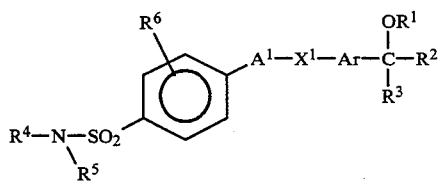

wherein $R^1$ is (1–4C) alkyl, (3–4C)alkenyl or (3–4C)alkynyl; and wherein $R^2$ and $R^3$ together form a group of the formula -$A^2$-$X^2$-$A^3$- which, together with the carbon atom to which $A^2$ and $A^3$ are attached, defines a ring having 5 or 6 ring atoms, wherein $A^2$ and $A^3$, which may be the same or different each is (1–3C)alkylene and $X^2$ is oxy, thio, sulphinyl or sulphonyl, and which ring may bear one or two substituents, which may be the same or different, selected from hydroxy, (1–4C)alkyl and (1–4C)alkoxy; wherein $A^1$ is a direct link to $X^1$ or is (1–3C)alkylene; wherein $X^1$ is oxy, thio, sulphinyl, sulphonyl or imino; wherein Ar is phenylene which may optionally bear one or two substituents selected from halogeno, hydroxy, amino, trifluoromethyl, (1–4C)alkyl and (1–4C)alkoxy; wherein $R^4$ is (1–4C)alkyl or fluoro (2–4C)alkyl, or $R^4$ is phenyl which may optionally bear one, two or three substituents selected from halogeno, hydroxy, amino, cyano, nitro, trifluoromethyl, carbamoyl, (1–4C) alkyl, (1–4C)alkoxy and (2–4C)alkanoylamino[, or $R^4$ is a 5- or 6-membered monocyclic heterocyclic moiety or a 9- or 10- membered by cyclic heterocyclic moiety each containing one or two nitrogen heteroatoms and each optionally containing a further heteroatom selected from nitrogen, oxygen and sulphur, or a hydrogenated derivative thereof, which heterocyclic moiety may optionally bear one or two substituents selected from halogeno, hydroxy, amino, cyano, nitro trifluoromethyl, carbamoyl, oxo, thioxo, (1–4C) alkyl, (1–4C) alkoxy and (2–4C) alkanoylamino]; $R^5$ is hydrogen or (1–4C) alkyl; and $R^6$ is hydrogen, halogeno, trifluoromethyl, (1–4C)alkyl or (1–4C) alkoxy; or a pharmaceutically-acceptable salt thereof.

2. A benzenesulphonamide derivative of the formula I as claimed in claim 1 wherein $X^1$ is oxy, thio or imino; or a pharmaceutically-acceptable salt thereof.

3. A benzenesulphonamide derivative of the formula I as claimed in claim 1 wherein $R^1$ is methyl, ethyl or allyl; $R^2$ and $R^3$ together form a group of the formula -$A^2$-$X^2$-$A^3$- which, together with the carbon atom to which $A^2$ and $A^3$ are attached, defines a ring having 5 or 6 ring atom, wherein $A^2$ and $A^3$ which may be the same or different, each is methylene, ethylene or trimethylene and $X^2$ is oxy, and which ring may bear one or two substituents selected from methyl and ethyl; $A^1$ is a direct link to $X^1$, or is methylene; $X^1$ is oxy or thio; Ar is 1,3-phenylene which may optionally bear one or two substituents selected from fluoro, chloro and trifluoromethyl; $R^4$ is methyl, ethyl or 2,2,2-trifluoroethyl, or $R^4$ is phenyl which may optionally bear one or two substituents selected from fluoro, chloro, cyano nitro and trifluoromethyl; $R^5$ is hydrogen or methyl; and $R^6$ is hydrogen, fluoro or chloro; or a pharmaceutically-acceptable salt thereof.

4. A benzenesulphonamide derivative of the formula I as claimed in claim 1 wherein $R^1$ is methyl; $R^2$ and $R^3$ together form a group of the formula -$A^2$-$X^2$-$A^3$- which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl substituent alpha to $X^2$; $A^1$ is a direct link to $X^1$ or is methylene; $X^1$ is oxy or thio; Ar is 1,3-phenylene which may optionally bear 1 or 2 fluoro substituents; $R^4$ is methyl, ethyl or 2,2,2-trifluoroethyl, or $R^4$ is phenyl which may optionally bear one or two substituents selected from fluoro, chloro and nitro $R^5$ is hydrogen or methyl; and $R^6$ is hydrogen; or a pharmaceutically-acceptable salt thereof.

5. A pharmaceutical composition which comprises a benzenesulphonamide derivative of the formula I, or a pharmaceutically-acceptable salt thereof, as claimed in any one of claims 1 to 4 in association with a pharmaceutically-acceptable diluent or carrier.

6. A method of treating a disease or medical condition mediated alone or in part by one or more leukotrienes which comprises administering to a warm-blooded animal requiring such treatment an effective amount of a benzenesulphonamide derivative of the formula I, or a pharmaceutically-acceptable salt thereof, as claimed in any one of claims 1 to 4.

* * * * *